US008791286B2

(12) United States Patent
Yodice et al.

(10) Patent No.: US 8,791,286 B2
(45) Date of Patent: Jul. 29, 2014

(54) PROCESS FOR MAKING SUBSTITUTED TRITHIOCARBONATE DERIVATIVES

(75) Inventors: Richard Yodice, Mentor, OH (US); John R. Johnson, Euclid, OH (US); Ross L. Beebe, Mentor, OH (US); Anthony J. Brzytwa, North Royalton, OH (US); Christopher D. Hilker, Norton, OH (US)

(73) Assignee: The Lubrizol Corporation, Wickliffe, OH (US)

( * ) Notice: Subject to any disclaimer, the term of this patent is extended or adjusted under 35 U.S.C. 154(b) by 802 days.

(21) Appl. No.: 12/669,996

(22) PCT Filed: Aug. 4, 2008

(86) PCT No.: PCT/US2008/072058
§ 371 (c)(1),
(2), (4) Date: Jun. 16, 2010

(87) PCT Pub. No.: WO2009/035793
PCT Pub. Date: Mar. 19, 2009

(65) Prior Publication Data
US 2010/0261927 A1    Oct. 14, 2010

Related U.S. Application Data

(60) Provisional application No. 60/954,852, filed on Aug. 9, 2007.

(51) Int. Cl.
*C07C 329/00* (2006.01)
*C08K 5/38* (2006.01)
(52) U.S. Cl.
USPC .......................................................... 558/243
(58) Field of Classification Search
CPC ................................. C07C 329/00; C08K 5/38
See application file for complete search history.

(56) References Cited

U.S. PATENT DOCUMENTS

| 2,021,726 | A | * | 11/1935 | Hess | 558/243 |
| 4,459,237 | A | * | 7/1984 | Bresson et al. | 558/243 |
| 4,528,141 | A | * | 7/1985 | Kimble et al. | 558/244 |
| 6,596,899 | B1 | | 7/2003 | Lai | |
| 6,894,116 | B2 | | 5/2005 | Lai | |
| 6,962,961 | B2 | | 11/2005 | Lai | |
| 7,038,062 | B2 | | 5/2006 | Parker | |
| 7,205,368 | B2 | * | 4/2007 | Lai | 526/286 |
| 7,230,063 | B1 | * | 6/2007 | Parker | 526/346 |
| 7,279,591 | B2 | * | 10/2007 | Lai | 558/240 |
| 7,335,788 | B2 | * | 2/2008 | Lai | 558/235 |
| 7,495,128 | B2 | * | 2/2009 | Lai | 562/581 |
| 7,632,966 | B2 | * | 12/2009 | Farnham | 562/28 |
| 7,956,211 | B2 | * | 6/2011 | Suau et al. | 558/243 |
| 2007/0123729 | A1 | * | 5/2007 | Farnham | 558/244 |
| 2008/0039651 | A1 | * | 2/2008 | Farnham | 562/426 |

FOREIGN PATENT DOCUMENTS

| WO | 01060792 | | 8/2001 | |
| WO | WO 01/60792 | * | 8/2001 | C07C 329/00 |

OTHER PUBLICATIONS

Hassner et al., Tetrahedron Letters, vol. 19, No. 46, pp. 4475-4478.*
Tucker et al., Applied Optics, vol. 45, No. 27, pp. 6973-6976.*
Search Report from corresponding PCT Application No. PCT/US2008/072058 dated Feb. 2, 2009.

* cited by examiner

*Primary Examiner* — Nyeemah A Grazier
(74) *Attorney, Agent, or Firm* — Christopher D. Hilker

(57) ABSTRACT

The present invention provides a low cost technique for synthesizing substituted trithiocarbonates and derivates thereof, by a one-step process which does not require solvent washes or re-crystallization steps, and results in practical yields more than double that of processes disclosed in the prior art.

13 Claims, No Drawings

PROCESS FOR MAKING SUBSTITUTED TRITHIOCARBONATE DERIVATIVES

FIELD OF THE INVENTION

The present invention relates to a process for making substituted trithiocarbonates and derivatives thereof. The compounds produced by the claimed invention can be utilized as initiators, chain transfer agents and/or terminators in controlled free radical polymerizations.

BACKGROUND OF THE INVENTION

Substituted trithiocarbonates and derivatives thereof are of commercial importance in a wide variety of applications, including their use as initiators, chain transfer agents and/or terminators in controlled free radical polymerizations.

Although several members of the class of organic trithiocarbonates have been known for many years and various routes have been employed for their synthesis, the process for making trithiocarbonate compounds in the present invention has not been disclosed.

Traditional methods of producing trithiocarbonates suffer many disadvantages, such as low conversion rates, high waste generation, slow reaction rates, the need for large amounts of solvents, the need for reagents to be charged in large excess, low practical yields where practical yield is defined as the weight percent calculated by dividing the total amount of trithiocarbonate compound collected from a process by the total amount of all materials charged over the course of the process and multiplying by one hundred to give a percent value, the need for expensive and time consuming solvent washes and re-crystallizations of the final product, and the cost and complexity of handling the final trithiocarbonate compounds, which are often a solid product. These disadvantages of the traditional methods of producing trithiocarbonates have resulted in no practical process or method capable of large-scale commercial use and so no large commercial source of trithiocarbonate compounds for any of their many commercial uses.

The process for producing trithiocarbonate compounds disclosed in the present invention alleviates the above noted problems and provides a commercially feasible means of producing trithiocarbonate compounds on a large scale.

U.S. Pat. No. 6,596,899, Lai, Jul. 22, 2003, discloses s,s'-bis(α,α'-disubstituted-α"-acetic acid)-trithiocarbonate and derivatives thereof and a process for making the same. The disclosed process is a multi-step process, requiring multiple reaction steps of the base used and the various reagents charged, where the first step combines carbon disulfide and a base to form an intermediate trithio structure and then a second step combines the intermediate with a haloform, a ketone and additional base. The disclosed examples involving the preparation of trithiocarbonates all require the product to be isolated and collected as a solid, and one of the examples requires a solvent re-crystallization step where additional solvent is added to the final mixture and the product is precipitated and then isolated as a solid. The examples result in practical yields, defined by the Applicants as the amount of product divided by the total amount of material charged over the process to obtain the product which is then multiplied by one hundred to give a percent, of 4.3% by weight or less. This maximum practical yield of 4.3% by weight in U.S. Pat. No. 6,596,899 is calculated by dividing the stated yield in example 2 of the reference of 40.3 grams of product by the sum of all charges made in the example, 942 grams.

U.S. Pat. No. 6,894,116, Lai et al., May 17, 2005 and U.S. Pat. No. 6,962,961, Lai, Nov. 8, 2005, have disclosures similar to U.S. Pat. No. 6,596,899, discussed above, including the same multi-step process for preparing the trithiocarbonate compounds and the same low practical yields.

U.S. Pat. No. 7,038,062, Parker, May 2, 2006 discloses a method for preparing cyclic trithiocarbonates from epoxides using an ionic liquid. The disclosed method allows for the re-use of the ionic liquid at least twice. All disclosed examples include re-crystallization steps to collect the final cyclic trithiocarbonates as crystalline solids and results in practical yields, as defined above, of 5.8% by weight or less.

The present invention provides an improved alternative to the processes discussed above for producing trithiocarbonate derivatives. The prior art uses multi-step reaction systems and re-crystallization steps to produce these compounds, with low practical yields, low conversion, and high waste generation. The claimed invention provides a simpler process with improved practical yield, improved conversion, higher purity and reduced waste generation. The claimed invention therefore solves the problems involved in producing these compounds on a commercial scale and provides a low cost means of making trithiocarbonate derivates.

SUMMARY OF THE INVENTION

The present invention provides a low cost technique for synthesizing substituted trithiocarbonates and derivatives thereof by a one-step process which does not require solvent washes or re-crystallization steps, and results in practical yields more than double that of processes disclosed in the prior art as well as high product purity and high conversion of the reactants to the desired products.

The present invention provides a process for reacting reagents: (i) $CS_2$, (ii) a haloform or reactive equivalent thereof, and (iii) a ketone or aldehyde of the structure $R^1C(=O)R^2$, and optionally (iv) a mercaptan of the structure $R^3SH$, wherein $R^1$, $R^2$ and $R^3$ are independently hydrogen or hydrocarbyl groups, provided that at least one of $R^1$, $R^2$ and $R^3$ is a hydrocarbyl group, to provide a trithiocarbonate acid product or of the general structure:

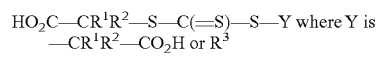

or a derivative thereof, said process comprising: (a) mixing, in a single vessel, reagents (i), (ii), (iii), optionally (iv) and (v) a metal hydroxide base, in an organic solvent in which said ketone or aldehyde, said haloform, and said trithiocarbonate product are soluble, and optionally with water; whereby the base naturalized form of the said trithiocarbonate product is formed from the reaction of the base (v) and the reagent (i) and the haloform (ii) and the ketone or aldehyde (iii) and the optional mercaptan (iv), and whereby an aqueous phase subsists along with an organic phase; (b) optionally removing the aqueous phase and any solids present at the end of step (a); (c) thereafter mixing with the mixture remaining in the vessel, an acid; whereby a trithiocarbonate acid is formed from the reaction of said trithiocarbonate and said acid, and whereby an aqueous phase subsists along with an organic phase; (d) optionally removing the aqueous phase and any solids present at the end of step (c); whereby an organic phase is provided in which said trithiocarbonate acid is dissolved; and (e) optionally isolating said trithiocarbonate acid from said organic phase of step (d); whereby impurities and reaction byproducts are removed from the reaction mixture in steps (b), (d) and (e).

The present invention provides a process for reacting reagents: (i) $CS_2$, (ii) a haloform The present invention further provides a process, as described above, wherein reagent (ii), the haloform, is chloroform, bromoform or mixtures thereof; the reagent (iii), the ketone or aldehyde, is acetone; the optional reagent (iv), the mercaptan, is dodecyl mercaptan; the reagent (v), the base, is sodium hydroxide, potassium hydroxide, or mixtures thereof; the organic solvent in step (a) is acetone, hexane, heptane or mixtures thereof; and the acid in step (c) is phosphoric acid, hydrochloric acid or mixtures thereof. The present invention also provides that the optional reagent (iv), the mercaptan, is replaced with a dialkyl amine.

One embodiment of the present invention provides for the process described, wherein optional steps (b) and (d) are independently carried out by liquid phase separation, draining, filtration or combinations thereof and optional step (e) is carried out by liquid phase separation, draining, filtration, flash stripping, kettle stripping, vacuum stripping or combinations thereof.

The present invention further provides for the process described above wherein the process further comprises: (f) mixing said trithiocarbonate acid with (vi) an alcohol of the structure $R^4$—OH where $R^4$ is a hydrocarbyl group; optionally an organic solvent; and optionally an acid catalyst in a reaction vessel; whereby a trithiocarbonate ester is formed from the reaction of said trithiocarbonate acid and said alcohol; and (g) optionally isolating said trithiocarbonate ester from said optional solvent, optional catalyst, and remaining alcohol.

In one embodiment of the present invention all of the steps of the process are independently carried out in a batch-wise manner. In another embodiment, one or more of steps (a), (b), (c), (d), (e), (f) and (g) are independently carried out in a continuous manner.

DETAILED DESCRIPTION OF THE INVENTION

Various preferred features and embodiments will be described below by way of non-limiting illustration.

The trithiocarbonates (TTCs) prepared by the claimed process, disclosed later herein, generally can be described in their acid state by the formulas:

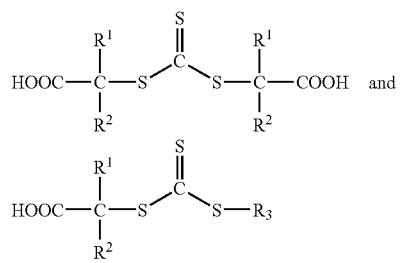

wherein $R^1$ and $R^2$ are independently hydrogen or a hydrocarbyl group, provided that at least one of $R^1$ and $R^2$ is a hydrocarbyl group, and wherein $R^3$ is a hydrocarbyl group.

The abbreviated reactions for the trithiocarbonates produced by the present invention can be generally written as follows:

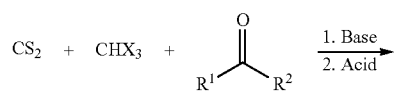

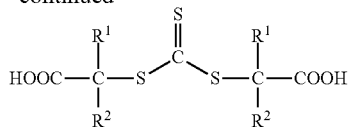

and

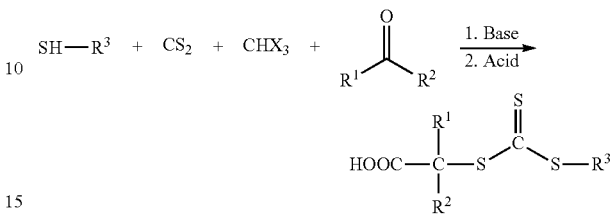

The present invention uses reagent (i) $CS_2$, (ii) a haloform, and (iii) a ketone or aldehyde of the structure $R^1C(=O)R^2$, and optionally (iv) a mercaptan of the structure $R^3SH$, wherein $R^1$ and $R^2$ are independently hydrogen or hydrocarbyl groups provided that at least one of $R^1$ and $R^2$ is a hydrocarbyl group, to provide the trithiocarbonate, and wherein $R^3$ is a hydrocarbyl group, in the presence of an optional organic solvent.

(i) The Carbon Disulfide.

The carbon disulfide, and/or the optional mercaptan, is generally the controlling reagent in the trithiocarbonate producing reaction. In general, the optional mercaptan may be the limiting reagent because of the potential for losses of carbon disulfide to the vent system. Other reactants may be used as the limiting reagent, depending on their relative amounts in the reaction mixture. The carbon disulfide may also be mixed with sodium sulfide, or reactive equivalents thereof such as a mixture of sodium hydroxide and hydrogen sulfide or a mixture of sodium hydrosulfide and sodium hydroxide, where the carbon disulfide and sodium sulfide or its equivalent are mixed at a molar ratio of about 1:1.

(ii) the Haloform.

The haloform used in the present invention has the general formula $CHX_3$ wherein each X is, independently, chlorine or bromine. The amount of haloform used in the present invention is generally from 1.0 to 20 moles of haloform per mole of carbon disulfide, in one embodiment from 1.3 to 3 moles of haloform per mole of carbon disulfide, and in another embodiment 1.8 to 2.5 moles of haloform per mole of carbon disulfide. Examples of haloforms include, but are not limited to, chloroform, bromoform and their reactive equivalents. In one embodiment of the present invention, compounds such as trichloroacetic acid may be used as a reactive equivalent to the haloform, where the compound breaks down in the reaction vessel and allows the reaction to proceed as described below.

(iii) The Ketone or Aldehyde.

Any ketone or aldehyde having the general formula:

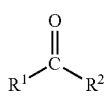

can be employed in the present invention, wherein $R^1$ and $R^2$, independently, can be the same or different, and can be hydrogen or a hydrocarbyl group. Examples of such compounds include acetone, formaldehyde, benzaldehyde, acetophenone, and methyl ethyl ketone. $R^1$ and $R^2$ can also form or be a part of a cyclic ring having from 5 to about 12 total carbon atoms. $R^1$ and $R^2$ are in one embodiment, independently, methyl or phenyl groups. As carbon disulfide is generally the controlling agent in the reaction, the ketone or aldehyde is generally used in an amount from 1 to 20 moles of ketone or aldehyde per mole of carbon disulfide, in one embodiment from 1 to 3 moles ketone or aldehyde per mole of carbon disulfide, and in one embodiment from 1.8 to 2.5 moles ketone or aldehyde per mole of carbon disulfide.

The ketone or aldehyde may also be used as the optional organic solvent in step (a), removing the need for a different solvent to be charged to the system. When the ketone or aldehyde is also used as the solvent, it is generally utilized in an amount of from generally 10 to 500 percent by weight of all reactants, and in another embodiment from about 50 percent to about 200 percent by weight of all reactants.

(iv) The Optional Mercaptan.

Any mercaptan having the general formula:

can be employed in the present invention, wherein $R^3$ may be a hydrocarbyl group, including both straight chain and branched chain hydrocarbyl groups. Typically, $R^3$ is a hydrocarbyl group containing 1 to 30 carbon atoms, and in one embodiment 1 to 20 carbon atoms, in another embodiment 5 to 15 carbon atoms and in another embodiment 8 to 14 carbon atoms. Examples of such compounds include, but are not limited to, methyl mercaptan, ethyl mercaptan, and the like, up to and including nonyl mercaptan, up to and including n-dodecyl mercaptan and tert-dodecyl mercaptan, and derivates of such mercaptans.

The mercaptan is generally used in an amount from about 0.5 to about 30 moles of mercaptan per mole of carbon disulfide and in another embodiment from about 1 to about 10 moles of mercaptan per mole of carbon disulfide, and in another embodiment from about 5 to 8 moles of mercaptan per mole of carbon disulfide.

(v) The Metal Hydroxide Base.

The metal hydroxide base suitable for use in the present invention includes, but is not limited to, sodium hydroxide, potassium hydroxide and mixtures thereof. In one embodiment of the present invention, the base may be a tetra-alkyl ammonium hydroxide solution, such as tetra-methyl ammonium hydroxide solution. The base is utilized in an amount generally from 1 to 15 moles of base per mole of carbon disulfide, and in another embodiment from 4 to 10 moles of base per mole of carbon disulfide utilized in the reaction.

The organic solvent present in step (a) may be any solvent in which the reagents (i), (ii), (iii) and (iv) and the trithiocarbonate intermediates and acid state are soluble. Suitable solvents include, but are not limited to, hydrohalomethylenes, particularly hydrochloromethylenes such as dichloromethane and trichloromethane; sulfolane, dibutyl ether, dimethyl sulfoxide, diisopropyl ether, di-n-propyl ether, 1,4-dioxane, tetrahydrofuran, benzene, toluene, hexane, carbon tetrachloride, heptane, xylene, mineral spirits and the like including mixtures thereof. In certain embodiments, solvents are heptanes or mineral spirits. The solvent, when present, is utilized in an amount generally from 10 to 500 percent by weight of all reactants, and in another embodiment from about 50 percent to about 200 percent by weight of all reactants.

The ketone or aldehyde (iii) may serve as some or all of the solvent. Where the ketone or aldehyde (iii) is serving as the solvent, no other organic solvent need be added.

The acids used in the acidification step, step (c), are typically mineral acids, which may include, but are not limited to, hydrochloric acid, sulfuric acid, and phosphoric acid. The acids are utilized in amounts suitable to make the solution at the end of step (c) acidic. In one embodiment, acid is added to the mixture until the system has a pH of less than 5, in other embodiments acid is added to a pH of 4, 3, and 2 or less.

The present invention comprises the steps of (a) mixing, in a single vessel, reagents (i), (ii), (iii), optionally (iv) and (v) a metal hydroxide base, in an organic solvent in which said ketone, said haloform, and said product are soluble; whereby a trithiocarbonate is formed from the reaction of the base (v) and the reagent (i) and the haloform (ii) and the ketone (iii) and the optional mercaptan (iv), and whereby an aqueous phase subsists along with a solvent phase; (b) optionally removing the aqueous phase and any solids present at the end of step (a); (c) mixing with the resulting mixture an aqueous acid or optionally adding water then aqueous acid; whereby a trithiocarbonate acid is formed from the reaction of said trithiocarbonate and said acid, and whereby an aqueous phase subsists along with a solvent phase; (d) optionally removing the aqueous phase and any solids present at the end of step (c); whereby an organic phase is provided in which said trithiocarbonate acid is dissolved; and (e) optionally isolating said trithiocarbonate acid from said organic phase; whereby impurities and reaction byproducts are removed from the reaction mixture in steps (b), (d) and (e).

Step (a), Forming the Trithiocarbonate.

The reagents: (i) the carbon disulfide, (ii) the haloform, (iii) the ketone or aldehyde, the optional organic solvent, and (iv) the optional mercaptan, are added to the reaction vessel. The reaction vessel and resulting mixture may be maintained at a temperature of about −15° C. to about 80° C. Some cooling of the reaction vessel, maintaining the temperature of about −15° C. to about 30° C. may be employed to reduce the amount of carbon disulfide, as well as the organic solvent and other reagents, lost to evaporation and/or flashing off the mixture if the reaction vessel is vented. Components (i), (ii), (iii) and optionally (iv) do not immediately react and can be held at this point before adding the base.

Then reagent (v), the base, is added to the reaction vessel, whereupon the exothermic reaction that forms the trithiocarbonate structure takes place in a single, one-step, process. During the base feed, the temperature of the mixture in the reaction vessel should be maintained at −15° C. to 80° C., for instance, about −5° C. to 25° C., or from 5° C. to 20° C. Temperatures below −15° C. may reduce the reaction rates involved in producing the trithiocarbonate to the point of increasing reaction times and even quenching the desired reactions. Temperatures above 80° C. may encourage the production of byproducts of the trithiocarbonate and intermediates thereof, reducing the final yield of product.

The reaction temperature, during step (a), can be controlled by cooling the reaction vessel, controlling the feed rate of the reagent (v) base being added, reflux cooling by controlling the pressure in the reaction vessel and so the boiling point of the organic solvent, using a side-arm cooler or equivalent heat exchanger, or combinations thereof. Additional means of cooling the reaction vessel would be evident to those skilled in the art.

A minor amount of water or acid may be added to the reaction vessel before, after or during the base addition. This optional water charge may be separate from any water that is added with the base, if the base is aqueous. The water may be used to adjust the reaction rate of a specific intermediate species formed in the reaction. That is, the formation and decomposition of 1,1,1-trichloro-2-methyl-2-propanol, otherwise known acetone chloroform or chloretone, which is a by-product from the chemical combination of acetone and chloroform, may impact the conversion of the reagents to the desired trithiocarbonate structure. The addition of water during the reaction step can help control these reaction rates and thus maximize conversion and yield. The water or acid catalyzed decomposition of chloretone may release large quantities of carbon monoxide. Any residual chloretone present should be decomposed before packaging or drumming the final reaction product or aqueous by-products in order to reduce and/or prevent carbon monoxide build-up in the holding containers.

A phase transfer catalyst may be added to the reaction mixture in step (a). The use of a phase transfer catalyst may be particularly useful if a solvent distinct from the ketone or aldehyde is used in the reaction and if multiple phases are present. When the ketone or aldehyde is utilized in the reaction as a reagent and as a solvent, no phase transfer catalyst is generally needed. The amount of phase transfer catalyst, when utilized in the present invention, is generally from 0.001 to 0.1 moles phase transfer catalyst per mole of carbon disulfide, in one embodiment from 0.005 to 0.5 moles per mole of carbon disulfide and in another embodiment from 0.02 to 0.04 moles per mole of carbon disulfide. The phase transfer catalysts can be a polyether, and/or an onium salt including a quaternary or tertiary organic compound of a nitrogen group element or an oxygen family element of the periodic table, and salts thereof. In one embodiment, the phase transfer catalysts are quaternary amines, and salts thereof e.g. quaternary ammonium hydroxides or halides While not wishing to be limited to any particular mechanism, it is believed that the specific mechanism for the reaction process, where the optional mercaptan is present, potassium hydroxide is used as the base and chloroform is used as the haloform, is as follows:

where reaction sequences I and II occur simultaneously and the resulting intermediates react in sequence III as soon as they are formed to create an exotherm. In one embodiment of the present invention the exotherm is delayed or latent relative to the charge of reagents to the system. That this complicated mechanism reacts to completion, with high conversion of the starting reagents to the desired trithiocarbonate, is a surprising result that is not suggested by the prior art, which is limited to multi-step reactions, where the counterparts to the sequences shown above are carried out at different times, and even in different reaction vessels.

In one embodiment of the present invention, (iv) the optional mercaptan may be replaced with a dialkyl amine, wherein the dialkyl amine has the structure: $R^4$—N(H)—$R^5$, wherein $R^4$ and $R^5$ are hydrocarbyl groups. In such an embodiment the reaction set forth in step I above would result in the same intermediate, and would proceed with the subsequent steps as shown, but would not require the initial mercaptan-base reaction, but would instead start with a reaction between the di-alkyl amine and carbon disulfide. Suitable dialkylamines for use in this invention include, but are not limited to, dialkylamines with alkyl groups containing 1 to 12 carbon atoms, such as dimethylamine.

Similarly, while again not wishing to be limited to any particular mechanism, it is believed that the specific mechanism for the reaction process, where the optional mercaptan is not present, sodium hydroxide is used as the base and chloroform is used as the haloform, is as follows:

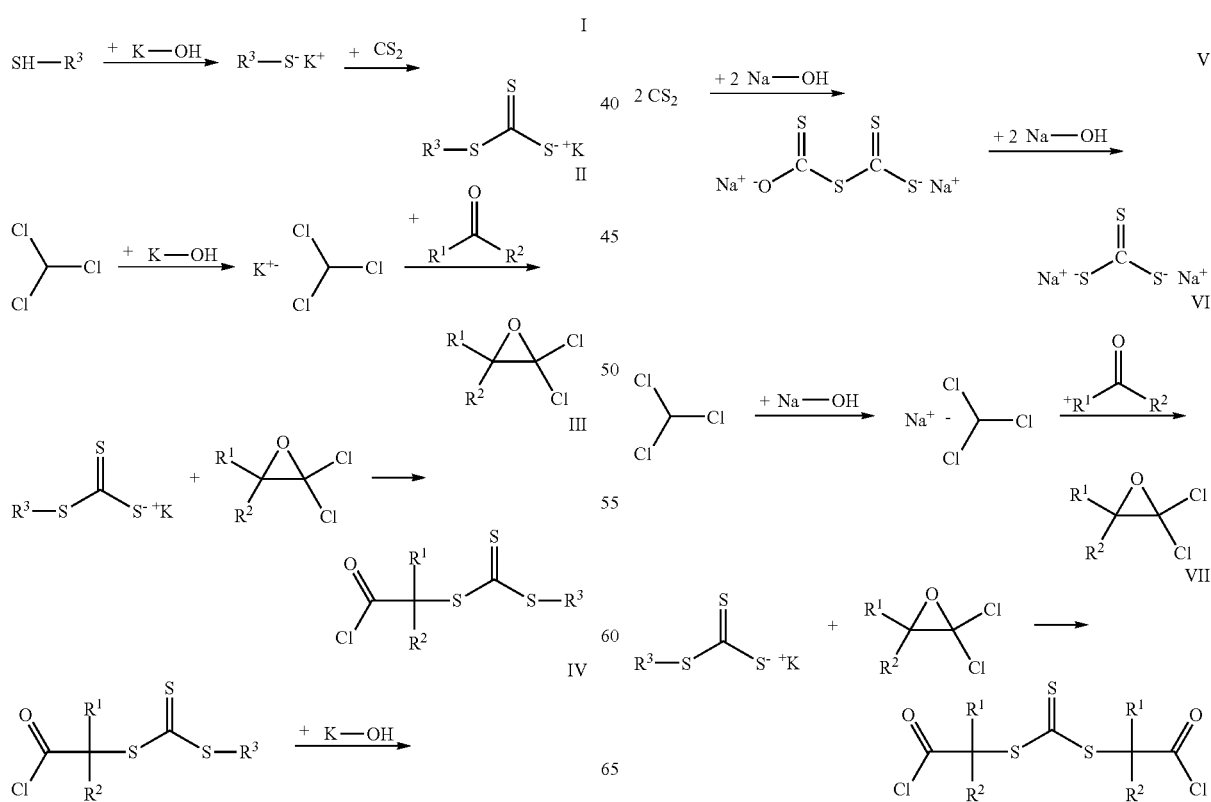

-continued

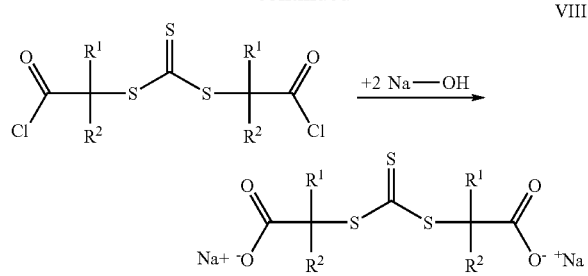

VIII where reaction sequences V and VI occur simultaneously and the resulting intermediates react in sequence VII as soon as they are formed. Again, that this mechanism reacts to completion with high conversion is a surprising result not suggested by the multi-step reactions of the prior art.

Potassium hydroxide and sodium hydroxide are shown as the base and chloroform is shown as the haloform in the mechanisms above for means of illustration. As described herein, additional bases and haloforms may be used in the present invention. Byproducts such as salt and water are not shown in the mechanisms above.

Step (a) results in the trithiocarbonate structure or derivative thereof as a salt. The reaction is completed in a single processing step, where all reagents are combined in the reaction vessel at the same time, and does not require the subsequent charges of the primary reagents to complete the reaction.

In one embodiment of the present invention, the reaction rates of the various reactions taking place in step (a) are controlled by controlling the solvent content of the reaction mixture and the specific solvents used in the reaction. Heptane and toluene can be used together as the optional organic solvent present in step (a). Controlling the ratio of heptane to toluene in the organic solvent can affect the reaction rates in step (a) effectively increasing or decreasing the overall reaction rate. This means of reaction rate control can be used in combination with the reaction management methods described above, as will be apparent to the person skilled in the art.

Step (b), Removing the Aqueous Phase and Solids.

Step (a) results in a mixture with an organic phase and an aqueous phase with the desired trithiocarbonate dissolved in the organic phase. The aqueous phase results from water generated by the reaction mechanism, any water added to the reaction vessel to help promote the desired reactions (as described above) and, if an aqueous base is used for reagent (v), water from the base addition. There may also be a large amount of salts, generated from the reaction, dissolved and in the aqueous phase and dropping out of the aqueous phase. These salts are formed from the reactions between the derivatives of the haloform and the metal hydroxide base. Specifically, the second reaction in reaction sequence II, and reaction sequence IV produce the salt present in the aqueous phase at the end of step (a). As excess base is generally added to drive the reactions to completion, the aqueous phase is generally basic.

The aqueous phase and salts may be optionally removed from the reaction vessel at this point. Methods of removal include, but are not limited to, phase separation by allowing the system to settle and draining the lower aqueous layer and salts, filtration to remove precipitated salts, centrifugation, liquid/liquid extraction, and combinations thereof.

Removing the aqueous layer and/or salts from the reaction vessel provides the benefit of a more product-concentrated mixture moving forward in the process and a reduced need for acid in the following acidification, due to the removal of the excess base. The aqueous layer may also contain by-products formed during the reaction and removing the layer acts to purify the product by removing these by-products.

Step (c), Forming the Trithiocarbonate Acid.

Step (c) involves the acidification of the mixture in the reaction vessel. An aqueous acid may be added to the reaction vessel, whereby the acid reacts with the trithiocarbonate formed in step (a) to form a trithiocarbonate acid. The reaction believed to be taking place and the resulting trithiocarbonate acid are illustrated below:

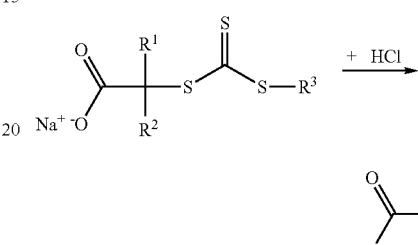

IX and

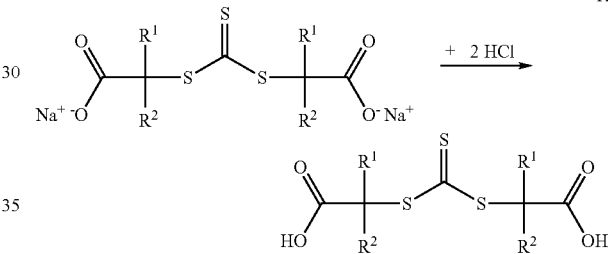

X where reaction sequence IX represents the reaction mechanism and product where the optional mercaptan is present and reaction sequence X represents the reaction mechanism and product where the optional mercaptan is absent.

Hydrochloric acid is shown as the acid in the mechanisms above for means of illustration. As described herein, additional acids (such as sulfuric acid) may be used in the present invention and in one embodiment the acids are aqueous. Byproducts such as salt and water are not shown in the mechanisms above.

The reaction vessel temperature may be controlled during step (c) to keep the mixture temperature at $-15°$ C. to $80°$ C., such as about $-5°$ C. to $25°$ C., or from $5°$ C. to $20°$ C. Temperatures below $-15°$ C. may reduce the reaction rates involved and may cause the product and possible byproducts to wax out or drop out of the organic component of the reaction vessel contents. Temperatures above $80°$ C. may encourage the decomposition of the trithiocarbonate and any remaining intermediates thereof, reducing the final yield of product.

Step (d), Removing the Aqueous Phase and Solids.

Step (c) results in a mixture with an organic phase and an aqueous phase with the desired trithiocarbonate dissolved in the organic phase. The aqueous phase results from water generated by the reaction mechanism and, if an aqueous acid is used, water from the acid addition. There may also be a large amount of salts, generated from the reaction, dissolved in and dropping out of any aqueous phase that may be present. These salts are formed from the reactions between the trithiocarbonate salt formed in step (a) and the acid charged in step (c). This reaction results in the formation of the trithiocarbonate acid and additional salts. As excess acid may be added to drive the conversion of the trithiocarbonate salt to the trithiocarbonate acid, residual acid may be present when the reaction is complete, whereby the aqueous phase may be acidic.

The aqueous phase and salts may be optionally removed from the reaction vessel at this point. Methods of removal include, but are not limited to, phase separation by allowing the system to settle and draining the lower aqueous layer and salts, filtration to remove precipitated salts, centrifugation, liquid/liquid extraction, and combinations thereof. Removing the aqueous layer and/or salts from the reaction vessel provides the benefit of a more product-concentrated mixture moving forward, such that it requires less storage volume and may be less corrosive (as the generally acidic aqueous layer is removed). The aqueous layer may also contain by-products formed during the reaction and removing the layer acts to purify the product by removing these by-products.

Step (e), Isolating the Product.

The trithiocarbonate product is present in the organic phase of the mixture present in the reaction vessel after the acidification. Isolating the product from the mixture may include, but is not limited to, removing any remaining aqueous layer, removing any salts, either dissolved in the aqueous layer or precipitating out of the solution, removing any remaining solvent and excess reactants present from step (a).

Aqueous layers and salts may be removed by means including, but not limited to, centrifugation, liquid/liquid extraction, water washes and phase separation draining, whereby the lower aqueous layer and salts are drained off the bottom of the reaction vessel, leaving the upper organic layer, containing the product, in the reaction vessel. Excess solvent and reagents may be removed by means including, but not limited to, kettle stripping, flash stripping, vacuum stripping, thin-film evaporation, fractionation, and combinations thereof, where said materials are boiled off of the reaction vessel. Other means may be used to isolate the product as well.

The isolation of the product is an optional step as the trithiocarbonate product is present in the mixture without isolation and may be usable in some applications where high purity is not a requirement. It may be desirable to isolate the product to in order to purify and concentrate the final product.

Water washes and solvent washes of the product may also be performed as part of the isolation of the product, however such steps are not required. Water or solvent may be charged to the reaction vessel and mixed with the mixture that contains the product. The contents of the reaction vessel may then be allowed to settle. The product may then be isolated from the washing material, which may also now contain residual byproducts, salts and excess reagents still present in the product-containing mixture.

The solvent used in solvent washes of the product may be a solvent or mixture of solvents in which the trithiocarbonate product is soluble or insoluble. If the product is soluble in the solvent, the isolation steps may include isolating the product containing mixture from the remaining by-product containing mixture and then stripping of the solvent to provide the product. The isolation steps may also include a filtration or re-crystallization step, however such a step is not required by the present invention. If the product is insoluble in the solvent used in any solvent wash, the isolation steps may include isolating the product containing mixture from the solvent and by-product containing mixture where the isolation may be completed by a phase separation, centrifugation, or liquid/liquid extraction.

Esterification.

The trithiocarbonate acid product produced by steps (a) through (e) may be further reacted with an alcohol to form a trithiocarbonate carboxylic ester (trithiocarbonate ester). These steps may be completed immediately after the trithiocarbonate acid has been formed or at some later time.

Step (f), Forming the Trithiocarbonate Ester.

The trithiocarbonate may be esterified in the same reaction vessel where steps (a) through (e) took place or in a separate reaction vessel. Any alcohol of the formula $R^4$—OH, where $R^4$ is a hydrocarbyl group, is suitable for use in this invention. Alcohols where $R^4$ is a hydrocarbyl group containing 2 to 30 carbon atoms, which is a primary, secondary or tertiary alcohol in nature, may be used, such as alcohols where $R^4$ is a hydrocarbyl group containing 4 to 12 carbon atoms. In one embodiment of the present invention, the alcohol used in the esterification is butyl alcohol or lauryl alcohol.

The amount of alcohol used in the esterification is generally from about 1 to 10 moles of alcohol per mole of trithiocarbonate acid to be converted to trithiocarbonate ester, in one embodiment from 1 to 5 moles per mole of trithiocarbonate acid to be converted to trithiocarbonate ester, and in another embodiment from 1 to 3 moles per mole of trithiocarbonate acid to be converted to trithiocarbonate ester.

The alcohol may be added to the trithiocarbonate acid and an optional organic solvent and an optional acid catalyst may be added as well. Suitable organic solvents for step (f) may be any solvent in which the trithiocarbonate acid and trithiocarbonate ester are soluble. Suitable solvents include, but are not limited to, sulfolane, dibutyl ether, dimethyl sulfone, diisopropyl ether, di-n-propyl ether, 1,4-dioxane, tetrahydrofuran, benzene, toluene, hexane, carbon tetrachloride, heptane, pentane, and mineral spirits including mixtures thereof. Suitable solvents thus include heptanes and mineral spirits. The solvent, when present, is utilized in an amount generally from 10 to 500 percent by weight of all reactants, and in another embodiment from 50 to 200 percent by weight of all reactants.

The optional acid catalyst may be para-toluene sulfonic acid or methanesulfonic acid. The amount of acid catalyst, when utilized in the present invention, is generally from 0.001 to 0.1 moles of acid catalyst per mole of trithiocarbonate acid to be converted to trithiocarbonate ester, in one embodiment from 0.005 to 0.5 moles per mole of trithiocarbonate acid to be converted to trithiocarbonate ester, and in another embodiment from 0.2 to 0.4 moles per mole of trithiocarbonate acid to be converted to trithiocarbonate ester.

Step (g), Isolating the Product.

The trithiocarbonate ester product is typically present in the organic phase of the mixture present in the reaction vessel after the esterification. Isolating the ester product from the mixture may include, but is not limited to, removing any remaining aqueous layer, removing any salts, either dissolved in the aqueous layer or precipitating out of the solution, removing any remaining solvent and excess reactants present from the prior steps.

Any aqueous layer and/or salts may be removed by methods including, but not limited to, centrifugation, liquid/liquid extraction, phase separation draining where the lower aqueous layer and salts are drained off the bottom of the reaction vessel, leaving the upper organic layer, containing the product. Excess solvent and reagents may be removed by methods including, but not limited to, kettle stripping, flash stripping, vacuum stripping, thin film evaporation, fractionation, and combinations thereof, where said non-product materials are boiled off of the reaction vessel. Other means may be used to isolate the product as well, as will be apparent to the person skilled in the art.

The isolation of the product is an optional step as the trithiocarbonate ester product is present in the mixture without isolation and may be usable as such in some applications where high purity is not a requirement. It may be desirable to isolate the ester product in order to purify and concentrate the final ester product.

Water washes and solvent washes of the ester product may also be performed as part of the isolation, however such steps are not required. Water or solvent may be charged to the reaction vessel and mixed with the mixture that contains the ester product. The contents of the reaction vessel may then be allowed to settle. The ester product may then be isolated from the washing material, which may also now contain residual byproducts, salts and excess reagents still present in the ester product-containing mixture.

The solvent used in solvent washes of the ester product may be a solvent or mixture of solvents in which the trithiocarbonate ester product is soluble or insoluble. If the product is soluble in the solvent, the isolation steps may include isolating the product containing mixture from the remaining by-product containing mixture and then stripping of the solvent to provide the product. The isolation steps may also include a filtration or re-crystallization step, however such a step is not required by the present invention. If the product is insoluble in the solvent used in any solvent wash, the isolation steps may include isolating the product containing mixture from the solvent and by-product containing mixture where the isolation may be completed by a phase separation, centrifugation, liquid/liquid extraction, and combinations thereof.

In one embodiment of the present invention, Step (a), Step (b), Step (c), Step (d), Step (e), Step (f) and Step (g) are carried out in a batch type process where the components of a step are added to and/or removed from one or more batch reaction vessels in amounts consistent with those described above and allowed to react to completion in one or more single batch reactions.

In another embodiment of the present invention, Step (a), Step (b), Step (c), Step (d), Step (e), Step (f), Step (g), or combinations thereof may be carried out in a continuous type process, where continuous flow rates of the various components are added to and/or removed from one or more continuous reaction vessels at flow rates corresponding to the relative amounts described above. Steps that are not completed in a continuous fashion may be completed in batch type process, with holding tanks, temporary intermediate storage, and similar processing steps used to transition the process to and/or from batch processing steps to continuous processing steps.

Permissible variations in the described process parameters will be apparent to the person skilled in the art.

As used herein, the term "hydrocarbyl substituent" or "hydrocarbyl group" is used in its ordinary sense, which is well-known to those skilled in the art. Specifically, it refers to a group having a carbon atom directly attached to the remainder of the molecule and having predominantly hydrocarbon character. Examples of hydrocarbyl groups include:

hydrocarbon substituents, that is, aliphatic (e.g., alkyl or alkenyl), alicyclic (e.g., cycloalkyl, cycloalkenyl) substituents, and aromatic-, aliphatic-, and alicyclic-substituted aromatic substituents, as well as cyclic substituents wherein the ring is completed through another portion of the molecule (e.g., two substituents together form a ring);

substituted hydrocarbon substituents, that is, substituents containing non-hydrocarbon groups which, in the context of this invention, do not alter the predominantly hydrocarbon nature of the substituent (e.g., halo (especially chloro and fluoro), hydroxy, alkoxy, mercapto, alkylmercapto, nitro, nitroso, and sulfoxy);

hetero substituents, that is, substituents which, while having a predominantly hydrocarbon character, in the context of this invention, contain other than carbon in a ring or chain otherwise composed of carbon atoms. Heteroatoms include sulfur, oxygen, nitrogen, and encompass substituents as pyridyl, furyl, thienyl and imidazolyl. In general, no more than two non-hydrocarbon substituent will be present for every ten carbon atoms in the hydrocarbyl group; typically, there will be no non-hydrocarbon substituents in the hydrocarbyl group.

EXAMPLES

Comparative Example 1

TTC Acid and Ester Preparation by Multi-Step Reaction Process

In a 5 L jacketed flask, equipped with a mechanical stirrer, a thermocouple, a reflux condenser and an addition funnel, the first part of a multi-step reaction process is carried out by adding 404.8 grams of dodecyl mercaptan, 1366 grams of acetone and 48.4 grams of Aliquat 336. The solution is stirred at 4° C. under a non-subline nitrogen purge while 168.0 grams of 50% sodium hydroxide solution is added over ~40 minutes, keeping the temperature below 20° C. After the addition, the flask is cooled below 10° C. Once cooled, the second step of the multi-step reaction is carried out by adding 152.0 grams of carbon disulfide to the flask over a 2 hour period while maintaining a temperature below 10° C. The carbon disulfide addition funnel is then flushed with an additional 199.0 grams of acetone into the flask. Following the flush, 358.1 grams of chloroform is added to the flask. The solution is mixed for 30 minutes while cooling back to 4° C.

Next, 800 grams of 50% sodium hydroxide solution is added to the flask over a 2 hour period, while maintaining the temperature below 27° C. The solution is then cooled to 10° C. and held overnight. The acetone is then removed by vacuum kettle stripping at 10° C. and 5.3 kPa (40 mmHg). After vacuum stripping, 2775 grams of distilled water and 332 grams 35% hydrochloric acid is added to the flask to reach a pH<2. The phases are mixed for five minutes and then allowed to separate, at which point the aqueous phase is drained. Once the phase separation is complete, 1500 grams of hexane is added to the flask and the mixture is heated to 52° C. At this point another phase separation is completed to ensure all water is removed. The hexane is then removed by vacuum kettle stripping at 68° C. and 5.3 kPa (40 mmHg). There are 300 grams of trithiocarbonate acid product recovered, giving a practical yield of 3.7% by weight, where practical yield is defined as the amount of product recovered divided by the sum of all materials added to the system and then multiplied by one hundred, here 300 grams of trithiocarbonate acid product divided by 8103.3 grams total charges.

For the ester reaction, 156.6 grams n-dodecyl alcohol and 7.9 grams methanesulfonic acid are added to the 300 grams of trithiocarbonate acid product, which is then heated to 110° C. Once the material reached 110° C., the material is held under those conditions for 4 hours while collecting water under reflux conditions. After 4 hours, the flask is cooled to 49° C. Next, 600 grams of isopropyl alcohol is added to the flask. The material is then cooled over night and filtered one pass through a Buchner funnel to collect 249.1 grams of trithiocarbonate ester product, giving a practical yield of 2.8% by weight, where practical yield is the total amount of product divided by the total amount of charges made to produce the product over the entire process, including the initial reaction(s) to produce the trithiocarbonate acid product, multiplied by one hundred, here 249.1 grams of trithiocarbonate ester product divided by 8867.8 grams total charges.

Example 2

TTC Acid and Ester Preparation by One Step Process

In a 570 L (150 gal) stainless steel reactor, a single reaction process step is completed by adding 20.4 kg (45 lbs) of dodecyl mercaptan, 151 kg (333 lbs) of acetone, 8.4 kg (18.5 lbs) carbon disulfide and 29.5 kg (65 lbs) of chloroform. The reactor pressure is reduced to about 33.3 kPa (250 mmHg). The solution is mixed at 4° C. while 125.2 kg (276 lbs) of 45% potassium hydroxide solution base is added over 1.5 hours, keeping the temperature below 21° C. After the base addition is complete, the reactor is cooled to near 4° C. while 151.0 kg (333 lbs) heptane, 68.0 kg (150 lbs) water, and then 65.8 kg (145 lbs) 35% hydrochloric acid is added to the reactor to reach a pH<2. The contents are mixed for 1 hour and then the agitation is stopped. After settling, a lower aqueous layer and solid salts are drained. After draining the phase separations, 158.8 kg (350 lbs) of water is added to the reactor and mixed for 15 minutes. The phase separation is repeated. The organic material is then transferred to a 380 L (100 gal) glass-lined reactor and then 113.4 kg (250 lbs) of water is added and mixed with the organic layer. The phases are again allowed to separate and the aqueous layer is drained. Lastly, the acetone is removed from the system by heating the system to 52° C. and holding at a system pressure of 5.3 kPa (40 mmHg). There are 68.2 kg (150.3 lbs) of trithiocarbonate acid product recovered, giving a practical yield, as defined above, of 7.6% by weight.

For the ester reaction, 36.3 kg (80 lbs) heptane, 18.6 kg (41 lbs) butanol and 3.9 kg (8.5 lbs) para-toluene sulfonic acid is added to the 68.2 kg (150.3 lbs) of stripped material in the 380 L (100 gal) reactor and then heated to 110° C. Once the material reaches 110° C., the material is held under those conditions for 12 hours while refluxing heptane and collecting water. After the 12 hour hold, the reactor is cooled to <66° C. After cooling, 19.5 kg (43 lbs) of 10% sodium bicarbonate solution is added to the reactor. After mixing for 5 minutes, the phases are allowed to separate and the lower aqueous phase is drained. After draining the aqueous layer, 158.8 kg (350 lbs) of water is added to the reactor and mixed for 15 minutes to water wash the product. The phase separation is repeated. Next, 158.8 kg (350 lbs) of water is added and mixed with the organic layer for a final wash. The phases are again allowed to separate and the aqueous layer is drained. Lastly, the material is vacuum kettle stripped at 85° C. and 5.3 kPa (40 mmHg). There are 38.1 kg (84.1 lbs) of trithiocarbonate ester product recovered, giving a practical yield, as defined above, of 3.0% by weight.

Example 3

TTC Acid and Ester Preparation by One Step Process

In a 1900 L (500 gal) stainless steel reactor, a single step reaction process is carried out by adding 66.7 kg (147 lbs) of dodecyl mercaptan, 494.4 kg (1090 lbs) of acetone, 27.7 kg (61 lbs) carbon disulfide and 97.5 kg (215 lbs) of chloroform. The reactor pressure is reduced to about 33.3 kPa (250 mmHg). The solution is mixed at 4° C. while 412 kg (908 lbs) of 45% potassium hydroxide base solution is added over 2.5 hours, keeping the temperature below 32° C. After the base addition is complete, the reactor is cooled to near 4° C. while 408.2 kg (900 lbs) heptane, 68.0 kg (150 lbs) water, and 215.9 kg (476 lbs) 35% hydrochloric acid are added to the reactor to reach a pH<2. The contents are mixed for 30 minutes and then the agitation is stopped. After settling, the lower aqueous layer and solid salts are drained. After draining the phase separations, 158.8 kg (350 lbs) of water is added to the reactor and the system is mixed for 15 minutes to water wash the material. The phase separation is repeated. The organic material is then transferred to a 380 L (100 gal) glass-lined reactor. Lastly, the solvent is removed by vacuum kettle stripping at 52° C. and 8.0 kPa (60 mmHg). There are 210.9 kg (465 lbs) of trithiocarbonate acid product recovered, with a practical yield, as defined above, of 10.8% by weight.

For the ester reaction, 120.2 kg (265 lbs) heptane, 61.2 kg (135 lbs) butanol and 12.7 kg (28 lbs) para-toluene sulfonic acid are added to the 210.9 kg (465 lbs) of trithiocarbonate acid material in the 380 L (100 gal) reactor, which is then heated to 110° C. Once the material reaches 110° C., the material is held under those conditions for 12 hours while refluxing heptane and collecting water. After the 12 hour hold, the reactor is cooled to <66° C. After cooling, 79.4 lbs (175 lbs) of 10% sodium bicarbonate solution is added to the reactor. After mixing for 5 minutes, the phases are allowed to separate and the lower aqueous phase is drained. After draining the aqueous layer, 158.8 kg (350 lbs) of water is added to the reactor and mixed for 15 minutes to water wash the material. The phase separation is repeated. Lastly, the material is vacuum kettle stripped at 85° C. and 5.3 kPa (40 mmHg). There are 123.8 kg (273 lbs) of trithiocarbonate ester product recovered, giving a practical yield, as defined above, of 5.2% by weight.

Example 4

TTC Acid and Ester Preparation by One Step Process

In a 1900 L (500 gal) stainless steel reactor, a one step reaction process is completed by adding 66.7 kg (147 lbs) of dodecyl mercaptan, 494.4 kg (1090 lbs) of acetone, 27.7 kg (61 lbs) carbon disulfide and 97.5 kg (215 lbs) of chloroform. The reactor pressure is reduced to about 33.3 kPa (250 mmHg). The solution is mixed at 4° C. while 411.9 kg (908 lbs) of 45% potassium hydroxide base solution is added over 1.5 hours, keeping the temperature below 21° C. After the base addition is complete, the reactor is cooled to near 21° C. and the reactor is brought to atmospheric pressure. The layers are then allowed to separate and the lower aqueous layer and solid salts are drained. Once the aqueous layer is drained, the organic material is then transferred to a 1900 L (500 gal) glass-lined reactor. Next, 181.4 kg (400 lbs) of water and 90.7 kg (200 lbs) of 35% hydrochloric acid is added to the reactor bringing the system to a pH of less than 2. The contents are mixed for 30 minutes and then the agitation is stopped, allowing the system to settle and the separation of a lower aqueous layer. The organic material containing the trithiocarbonate acid product is then drummed and saved for composite stripping and esterification.

The above process is repeated two more times, for a total of three reactions. The second reaction uses the same charges listed above except that 90.7 kg (200 lbs) of water and 45.4 kg (100 lbs) of hydrochloric acid is used, instead of 181.4 kg (400 lbs) and 90.7 kg (200 lbs) respectively. The third reaction is scaled up by about 20% compared to the first reaction and used 81.2 kg (179 lbs) dodecyl mercaptan, 593.3 kg (1308 lbs) acetone, 33.1 kg (73 lbs) carbon disulfide, 117.0 kg (258 lbs) chloroform, 484.0 kg (1067 lbs) 45% potassium hydroxide, 108.9 kg (240 lbs) of water and 54.4 kg (120 lbs) of hydrochloric acid. Other than the differences in charges discussed, the same procedures described for the first reaction above is used in the second and third reactions.

When the three reactions are complete, the collected organic material containing the trithiocarbonate acid product from all three reactions is then combined in the 1900 L (500 gal) glass-lined reactor. The acetone is then removed from the system by vacuum kettle stripping at 52° C. and 8.0 kPa (60 mmHg). There are 730.7 kg (1611 lbs) of trithiocarbonate acid product recovered, giving a practical yield, as defined above, of 17.9% by weight.

For the ester reaction, 381.0 kg (840 lbs) heptane, 196.0 kg (432 lbs) butanol and 40.8 kg (90 lbs) para-toluene sulfonic acid is added to the stripped material and then heated to 110° C. Once the material reaches 110° C., the material is held under those conditions for 16 hours while refluxing heptane and collecting water. After the 16 hour hold, the reactor is cooled to <66° C. After cooling, 147.9 kg (326 lbs) of 10% sodium bicarbonate solution is added to the reactor. After mixing for 5 minutes, the phases are allowed to separate and the lower aqueous phase is drained. After draining the aqueous layer, 158.8 kg (350 lbs) of water is added to the reactor and the system is mixed for 15 minutes to water wash the product. The phase separation is repeated. Lastly, the material is vacuum kettle stripped at 85° C. and 5.3 kPa (40 mmHg). There are 415.5 kg (916 lbs) of trithiocarbonate ester product recovered, giving a practical yield, as defined above, of 8.3% by weight.

Example 5

TTC Acid and Ester Preparation by One Step Process

In a 1900 L (500 gal) stainless steel reactor, a one step reaction process is completed by adding 100.2 kg (221 lbs) of dodecyl mercaptan, 743.9 kg (1640 lbs) of acetone, 41.7 kg (92 lbs) carbon disulfide and 146.5 kg (323 lbs) of chloroform. The reactor pressure is reduced to about 33.3 kPa (250 mmHg). The solution is mixed at 4° C. while 553.4 kg (1220 lbs) of 45% potassium hydroxide base solution is added over 4 hours, keeping the temperature below 32° C. After the base addition is complete, the reactor is cooled to near 21° C. and the reactor is brought to atmospheric pressure. The layers are then allowed to separate and the lower aqueous layer and solid salts are drained. Once the aqueous layer is drained, the organic material is then transferred to a 1900 L (500 gal) glass-lined reactor. Next, 79.4 kg (175 lbs) water and 56.7 kg (125 lbs) 35% hydrochloric acid are added to the reactor to reach a pH<2. The contents are mixed for 30 minutes and then the agitation is stopped, allowing the system to settle and for the separation of a lower aqueous layer, which is removed. The organic material containing the trithiocarbonate acid product is then drummed and saved for composite stripping and esterification. The above process is repeated two more times, for a total of three reactions, with the only difference between the reactions being the use of 113.4 kg (250 lbs) of water and 56.7 kg (125 lbs) of hydrochloric acid in the second reaction and 113.4 kg (250 lbs) of water and 69.4 kg (153 lbs) hydrochloric acid in the third reaction. The collected organic material containing the trithiocarbonate acid product from all three reactions is then combined in the glass-lined reactor. The acetone is then removed from the system by vacuum kettle stripping at 52° C. and 5.3 kPa (40 mmHg). There are 880.0 kg (1940 lbs) of trithiocarbonate acid product recovered, giving a practical yield, as defined above, of 16.8% by weight.

For the ester reaction, 272.2 kg (600 lbs) heptane, 276.2 kg (609 lbs) butanol and 57.2 kg (126 lbs) para-toluene sulfonic acid is added to the 880.0 kg (1940 lbs) of stripped material, which is then heated to 110° C. Once the material reaches 110° C., the material is held under those conditions for 12 hours while refluxing heptane and collecting water. After the 12 hour hold, the reactor is cooled to <66° C. After cooling, 149.7 kg (330 lbs) of 10% sodium bicarbonate solution is added to the reactor. After mixing for 5 minutes, the phases are allowed to separate and the lower aqueous phase is drained. Lastly, the material is stripped at 85° C. and 5.3 kPa (40 mmHg). There are 597.2 kg (1316.5 lbs) of trithiocarbonate ester product recovered, giving a practical yield, as defined above, of 10.0% by weight.

Example 6

TTC Acid and Ester Preparation by One Step Process

In a 12 L jacketed flask, equipped with a mechanical stirrer, a thermocouple, a reflux condenser and an addition funnel, a one step reaction process is completed by adding 626 grams of dodecyl mercaptan, 5052 grams of acetone, 260 grams carbon disulfide and 915 grams of chloroform. The solution is stirred at 10° C. under a non-subline nitrogen purge while 3480 grams of 45% potassium hydroxide base solution is added over 3 hours, keeping the temperature below 32° C. After the addition, the flask is maintained near 32° C. The phases are then allowed to separate and the lower aqueous layer and solid salts are drained. After draining the aqueous layer, 1136 grams of water and 568 grams 35% hydrochloric acid are added to the flask to reach a pH of less than 2. The phases are again allowed to separate and the aqueous phase is drained. Lastly, the acetone is removed by vacuum kettle stripping at 66° C. and 2.7 kPa (20 mmHg). There are 6009 grams of trithiocarbonate acid product recovered, giving a practical yield, as defined above, of ~49.9% by weight.

For the ester reaction, 417 grams heptane, 425 grams butanol and 87 grams methanesulfonic acid are added to the 6009 grams of stripped trithiocarbonate acid material, which is then heated to 110° C. Once the material reaches 110° C., the material is held under those conditions for 12 hours while collecting water. After 4 hours, the flask is cooled to <66° C. After cooling, 556 grams of a 10% sodium bicarbonate solution is added to the flask. After mixing for 5 minutes, the phases are allowed to separate and the lower aqueous phase is drained. Lastly, the material is stripped at 85° C. and 2.7 kPa (20 mmHg). There are 1300 grams of trithiocarbonate ester product recovered, giving a practical yield, as defined above, of 9.6% by weight.

Example 7

TTC Acid Preparation by One Step Process

In a 12 L jacketed flask, equipped with a mechanical stirrer, a thermocouple, a reflux condenser and an addition funnel, a one step reaction process is carried out by adding 673 grams of dodecyl mercaptan, 4495 grams of acetone, 280 grams carbon disulfide and 982 grams of chloroform. The solution is stirred at 10° C. under a non-subline nitrogen purge while 3321 grams of 45% potassium hydroxide solution is added over 3.5 hours, keeping the temperature below 32° C. After the addition, the flask is maintained near 32° C. The phases are then allowed to separate and the lower aqueous layer and solid salts are drained. After draining the aqueous layer, 915 grams of water and 457 grams 35% hydrochloric acid is added to the flask to reach a pH of less than 2. The phases are again allowed to separate and the aqueous phase is drained. Lastly, the acetone is removed by vacuum kettle stripping at 66° C. and 2.7 kPa (20 mmHg). There are 2549 grams of trithiocarbonate acid product recovered, giving a practical yield, as defined above, of 22.9% by weight.

Example 8

TTC Acid Preparation by One Step Process

In a 1900 L (500 gal) stainless steel reactor, a one step reaction process is carried out by adding 108.0 kg (238 lbs) of dodecyl mercaptan, 859.1 kg (1894 lbs) of acetone, 53.5 kg (118 lbs) carbon disulfide and 187.8 kg (414 lbs) of chloroform. The reactor pressure is reduced to about 33.3 kPa (250 mmHg). The solution is mixed at 4° C. while 635.0 kg (1400 lbs) of 45% potassium hydroxide base solution is added over 4 hours, keeping the temperature below 32° C. After the base addition is complete, the reactor is brought to atmospheric pressure. Next, 163.3 kg (360 lbs) of water is charged to the reactor and mixed for 10 minutes. The layers are then allowed to separate and the lower aqueous layer and solid salts are drained. Once the aqueous layer is drained, the organic material is then transferred to a 1900 L (500 gal) glass-lined reactor. Next, 163.3 kg (360 lbs) water and 81.6 kg (180 lbs) 35% hydrochloric acid are added to the reactor to obtain a pH of less than 2. The contents are mixed for 30 minutes and then the agitation is stopped and the system is allowed to settle and separate an aqueous layer. The trithiocarbonate acid containing organic material is then drummed and transferred to a 3800 L (1000 gal) stainless steel reactor for composite stripping. This process is then repeated 7 more times. In the 3800 L (1000 gal) reactor, containing the trithiocarbonate acid containing organic material from all seven one step reactions, the acetone is removed by vacuum kettle stripping at 66° C. and 2.7 kPa (20 mmHg). There are 2137.8 kg (4713 lbs) of trithiocarbonate acid product recovered, giving a practical yield, as defined above, of 13.6% by weight.

Example 9

TTC Acid Preparation by Continuous One Step Process

In a 12 L flask, called "feed flask 1", equipped with a mechanical stirrer, a thermocouple, a reflux condenser and an addition funnel, 905.2 grams of dodecyl mercaptan, 6721.6 grams of acetone, 376.4 grams carbon disulfide and 1321.9 grams of chloroform are added. An identical second 12 L flask, called "feed flask 2", is filled with 15,768 grams of 45% potassium hydroxide solution.

In a 5 L jacketed flask, called the "reaction flask", equipped with a mechanical stirrer, a thermocouple, a reflux condenser and an addition funnel, ~4200 grams unstripped trithiocarbonate acid product from example 3 is added as a product heel. The solution in the reaction flask is stirred and circulated at 21° C. under a non-subline nitrogen purge. A continuous one step reaction process to produce trithiocarbonate acid product is then carried out by adding the materials from the two 12 L feed flasks to the 5 L reaction flask at a rate of 41.4 grams per minute total, wherein the potassium hydroxide solution in feed flask 2 is fed at 15.5 grams per minute and the organic mixture in feed flask 1 is fed at 25.9 grams per minute. The temperature is maintained near 21° C. during these continuous feeds.

The 5 L reaction flask is also equipped with a subline tube that is connected to a 12 L "collection flask" via a MasterFlex pump. The pump is pre-calibrated to withdraw about 41.4 grams per minute of the reaction mixture from the 5 L reaction flask and charge it to the 12 L collection flask. The process is continuously run in this fashion until raw materials in the 12 L feed flasks are exhausted. The 12 L collection flask is periodically drained to allow room for more product-containing material. Material from the collection flask is charged to a 12 L system as described in example 6. The material is allowed to phase separate and the lower aqueous layer and solid salts are drained, at which point the material is worked up to a final trithiocarbonate acid product following the same procedure set out in example 6. The continuous process effectively produces about 4.5 grams of trithiocarbonate acid product per minute, and relative to the 41.4 grams per minute total feed rate, gives a practical yield, as defined above, of 10.7% by weight.

TABLE 1

Practical Yield Data

| Example | Practical Yield of TTC Acid (% by weight) | Practical Yield of TTC Ester (% by weight) |
| --- | --- | --- |
| 1 (comparative) | 3.7% | 2.8% |
| 2 | 7.6% | 3.0% |
| 3 | 10.8% | 5.2% |
| 4 | 17.9% | 8.3% |
| 5 | 16.8% | 10.0% |
| 6 | 49.9% | 9.6% |
| 7 | 22.9% | — |
| 8 | 13.6% | — |
| 9 | 10.7% | — |

The data shows that all examples using the reaction process of the present invention have higher practical yields for both the trithiocarbonate acid and trithiocarbonate ester products compared to the comparative example, which uses a more conventional, multi-step reaction process.

Each of the documents referred to above is incorporated herein by reference. Except in the Examples, or where otherwise explicitly indicated, all numerical quantities in this description specifying amounts of materials, reaction conditions, molecular weights, number of carbon atoms, and the like, are to be understood as modified by the word "about." Unless otherwise indicated, each chemical or composition referred to herein should be interpreted as being a commercial grade material which may contain the isomers, by-products, derivatives, and other such materials which are normally understood to be present in the commercial grade. However, the amount of each chemical component is presented exclusive of any solvent or diluent oil, which may be customarily present in the commercial material, unless otherwise indicated. It is to be understood that the upper and lower amount, range, and ratio limits set forth herein may be independently combined. Similarly, the ranges and amounts for each element of the invention can be used together with ranges or amounts for any of the other elements. As used herein, the expression "consisting essentially of" permits the inclusion of substances that do not materially affect the basic and novel characteristics of the composition under consideration. The term "minor amount" means an amount of less than 50% of the substance in question as a fraction of the total composition unless otherwise indicated above. The term "major amount" means an amount of 50% or more of the substance in question as a fraction of the total composition unless otherwise indicated above.

What is claimed is:

1. A process for reacting reagents: (i) $CS_2$, (ii) a haloform or reactive equivalent thereof, and (iii) a ketone or aldehyde of the structure $R^1C(\!=\!O)R^2$, and optionally (iv) a mercaptan of the structure $R^3SH$, wherein $R^1$, $R^2$ and $R^3$ are independently hydrogen or hydrocarbyl groups, provided that at least one of $R^1$ and $R^2$ is a hydrocarbyl group, and wherein $R^3$ is a hydrocarbyl group, to provide a trithiocarbonate acid product of the general structure:

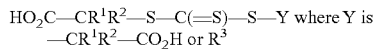

$HO_2C\text{—}CR^1R^2\text{—}S\text{—}C(\!=\!S)\text{—}S\text{—}Y$ where Y is $\text{—}CR^1R^2\text{—}CO_2H$ or $R^3$ said process comprising:
- (a) mixing, in a single vessel, reagents (i), (ii), (iii), and (iv) when present, where the resulting mixture is free of any base reagent, and then, after mixing reagents (i), (ii), (iii), and (iv) when present, adding to the vessel (v) a metal hydroxide base, in an organic solvent in which said ketone or aldehyde, said haloform, and said trithiocarbonate product are soluble; whereby the base-neutralized form of said trithiocarbonate product is formed from the reaction of the base (v) and the mixture of reagent (i) and the haloform (ii) and the ketone or aldehyde (iii) and the optional mercaptan (iv), and whereby an aqueous phase subsists along with an organic phase;
- (b) optionally removing the aqueous phase and any solids present at the end of step (a);
- (c) thereafter mixing with the mixture remaining in the vessel, an acid; whereby a trithiocarbonate acid is formed from the reaction of said trithiocarbonate and said acid, and whereby an aqueous phase subsists along with an organic phase;
- (d) optionally removing the aqueous phase and any solids present at the end of step (c); whereby an organic phase is provided in which said trithiocarbonate acid is dissolved; and
- (e) optionally isolating said trithiocarbonate acid from said organic phase of step (d).

2. The process of claim 1 wherein reagent (ii), the haloform, is chloroform, bromoform or mixtures thereof; the reagent (iii), the ketone or aldehyde, is acetone; the optional reagent (iv), the mercaptan, contains 8 to 14 carbon atoms; the reagent (v), the base, is sodium hydroxide, potassium hydroxide, or mixtures thereof; the organic solvent in step (a) is acetone, hexane, heptane, toluene or mixtures thereof; and the acid in step (c) is phosphoric acid, hydrochloric acid or mixtures thereof.

3. The process of claim 1 wherein step (a) further includes mixing a dialkyl amine in with the reagents.

4. The process of claim 1 wherein step (a) is carried out with the reaction vessel maintained at a temperature of about $-15°$ C. to about 80° C.

5. The process of claim 1 wherein optional steps (b) and (d) are independently carried out by liquid phase separation, draining, filtration or combinations thereof and optional step (e) is carried out by liquid phase separation, draining, filtration, flash stripping, kettle stripping, vacuum stripping or combinations thereof.

6. The process of claim 1 wherein step (c) is carried out with the reaction vessel maintained at a temperature of about $-15°$ C. to about 80° C.

7. A process for reacting reagents: (i) $CS_2$, (ii) a haloform or reactive equivalent thereof, and (iii) a ketone or aldehyde of the structure $R^1C(\!=\!O)R^2$, and optionally (iv) a mercaptan of the structure $R^3SH$, wherein $R^1$, $R^2$ and $R^3$ are independently hydrogen or hydrocarbyl groups, provided that at least one of $R^1$ and $R^2$ is a hydrocarbyl group, and wherein $R^3$ is a hydrocarbyl group, to provide a trithiocarbonate acid product of the general structure:

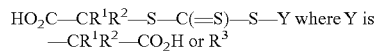

$HO_2C\text{—}CR^1R^2\text{—}S\text{—}C(\!=\!S)\text{—}S\text{—}Y$ where Y is $\text{—}CR^1R^2\text{—}CO_2H$ or $R^3$ where said trithiocarbonate acid is then further reacted with (vi) an alcohol to provide a trithiocarbonate ester, said process comprising:
- (a) mixing, in a single vessel, reagents (i), (ii), (iii), and (iv) when present, where the resulting mixture is free of any base reagent, and then, after mixing reagents (i), (ii), (iii), and (iv) when present, adding to the vessel (v) a metal hydroxide base, in an organic solvent in which said ketone or aldehyde, said haloform, and said trithiocarbonate product are soluble; whereby the base-neutralized form of said trithiocarbonate product is formed from the reaction of the base (v) and the mixture of reagent (i) and the haloform (ii) and the ketone or aldehyde (iii) and the optional mercaptan (iv), and whereby an aqueous phase subsists along with an organic phase;
- (b) optionally removing the aqueous phase and any solids present at the end of step (a);
- (c) thereafter mixing with the mixture remaining in the vessel, an acid; whereby a trithiocarbonate acid is formed from the reaction of said trithiocarbonate and said acid, and whereby an aqueous phase subsists along with an organic phase;
- (d) optionally removing the aqueous phase and any solids present at the end of step (c); whereby an organic phase is provided in which said trithiocarbonate acid is dissolved; and
- (e) optionally isolating said trithiocarbonate acid from said organic phase of step (d);

wherein the process further comprises:
- (f) mixing said trithiocarbonate acid with (vi) an alcohol wherein said alcohol has the structure $R^4\text{—}OH$ where $R^4$ is a hydrocarbyl group; optionally a organic solvent; and optionally an acid catalyst in a reaction vessel; whereby a trithiocarbonate ester is formed from the reaction of said trithiocarbonate acid and said alcohol; and
- (g) optionally isolating said trithiocarbonate ester from said optional solvent, optional catalyst, and remaining alcohol.

8. The process of claim 7 wherein the esterification is carried out with the reaction vessel maintained at a temperature of about $-15°$ C. to about 80° C.

9. The process of claim 7 wherein steps (a), (b), (c), (d), (e), (f) and (g) are independently carried out in a batch-wise manner;

wherein the reagents are used in the completion of the steps such that there are 1 to 20 moles of (ii) haloform, 1 to 20 moles of (iii) ketone or aldehyde, 0.5 to 30 moles of (iv) mercaptan, and 1 to 15 moles of (v) base, used per mole of (i) carbon disulfide used; and 1 to 10 moles of (vi) alcohol are used per mole of trithiocarbonate acid to be converted to trithiocarbonate ester.

10. The process of claim 7 wherein one or more of steps (a), (b), (c), (d), (e), (f) and (g) are independently carried out in a continuous manner;
wherein the reagents are used in the completion of the steps such that there are 1 to 20 moles of (ii) haloform, 1 to 20 moles of (iii) ketone or aldehyde, 0.5 to 30 moles of (iv) mercaptan, and 1 to 15 moles of (v) base, used per mole of (i) carbon disulfide used; and 1 to 10 moles of (vi) alcohol are used per mole of trithiocarbonate acid to be converted to trithiocarbonate ester.

11. The process of claim 1 wherein water is added to the reaction mixture in step (a), before, during or after the addition of component (v) the metal hydroxide base.

12. A process for producing a trithiocarbonate acid of the general structure:

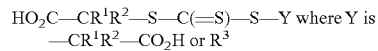

wherein $R^1$, $R^2$ and $R^3$ are independently hydrogen or hydrocarbyl groups, provided that at least one of $R^1$ and $R^2$ is a hydrocarbyl group, and wherein $R^3$ is a hydrocarbyl group;
wherein said process comprises:
(I) preparing a mixture consisting essentially of: (i) $CS_2$, (ii) a haloform or reactive equivalent thereof, (iii) a ketone or aldehyde of the structure $R^1C(=O)R^2$, and (iv) an optional mercaptan of the structure $R^3SH$, and then reacting the mixture with (v) a metal hydroxide base; wherein the reaction of components (i), (ii), (iii), (iv) when present, and (v), which produces a trithiocarbonate; and
(II) reacting said trithiocarbonate with an acid, which produces said trithiocarbonate acid.

13. A process for producing a trithiocarbonate ester wherein said process comprises the esterification of a trithiocarbonate acid of the general structure:

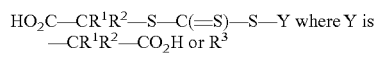

wherein $R^1$, $R^2$ and $R^3$ are independently hydrogen or hydrocarbyl groups, provided that at least one of $R^1$ and $R^2$ is a hydrocarbyl group, and wherein $R^3$ is a hydrocarbyl group;
wherein said process comprises
(I) preparing a mixture consisting essentially of: (i) $CS_2$, (ii) a haloform or reactive equivalent thereof, (iii) a ketone or aldehyde of the structure $R^1C(=O)R^2$, and (iv) an optional mercaptan of the structure $R^3SH$, and then reacting the mixture with (v) a metal hydroxide base; wherein the reaction of components (i), (ii), (iii), (iv) when present, and (v), which produces a trithiocarbonate; and
(II) reacting said trithiocarbonate with an acid, which produces said trithiocarbonate acid; and
(III) mixing said trithiocarbonate acid with (vi) an alcohol wherein said alcohol has the structure $R^4$—OH where $R^4$ is a hydrocarbyl group; whereby said trithiocarbonate ester is formed from the reaction of said trithiocarbonate acid and said alcohol.

* * * * *